US00PP12160P2

(12) United States Plant Patent
Heims

(10) Patent No.: US PP12,160 P2
(45) Date of Patent: Oct. 23, 2001

(54) HUECHERA PLANT NAMED 'AUTUMN HAZE'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/452,025

(22) Filed: Nov. 30, 1999

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A Para
(74) *Attorney, Agent, or Firm*—Klarquist Sparkman Campbell Leigh & Whinston LLP

(57) ABSTRACT

A new and distinct hybrid of Heuchera plant characterized by a unique combination of mint-green leaves with a pinkish-purple cast and compact form.

1 Drawing Sheet

The present invention relates to a new and distinct hybrid of Heuchera, of the family Saxifragaceae, which originated as a cross between an unpatented Heuchera named 'French Velvet' (seed parent) and an unpatented, unnamed Heuchera hybrid seedling (pollen parent). Due to the fact that the instant plant and parent plants are the result of crosses between several different Heuchera species, no species designations are given.

This new Heuchera is a result of a controlled cross of the aforementioned plants in Canby, Oreg. This hybrid was selected from a large selection of seedlings. Seed and pollen parent plants were retained to observe habit and to compare with the instant plant. The new variety has been reproduced only by asexual propagation (division and tissue culture). Each of the progeny exhibits identical characteristics to the original plant.

This plant is characterized by the following:

1. Mint-green foliage with a pinkish-purple cast.
2. Compact form as a result of short petioles.

Asexual propagation by division and tissue culture as done in Canby, Oreg., shows that the foregoing characteristics and distinctions come true to form and are established and transmitted through succeeding propagations.

BRIEF DESCRIPTION OF THE DRAWING

The drawing shows Heuchera 'Autumn Haze' in April in Canby, Oreg.

DETAILED PLANT DESCRIPTION

The following is a detailed description of the new Heuchera hybrid based on observations of one and a half year old specimens in the field in Canby, Oreg. The color descriptions are all based on the *Royal Horticultural Society Colour Chart.*

Foliage:
- *Type.*—Simple. Evergreen.
- *Shape.*—Cordate. Palmately cleft.
- *Length.*—7.5 cm.
- *Width.*—9.5 cm.
- *Petiole length.*—9 cm.
- *Margins.*—Dentate-doubly-serrate. Undulate. Ciliolate.
- *Apex.*—Broadly acute. Almost rounded.
- *Base.*—Cordate.

- *Leaf texture.*—Upper and lower surface are puberulent. Under surface veins are velutinous.
- *Petiole texture.*—Villous.
- *Leaf arrangement.*—Rosette.
- *Venation.*—Reticulate.

Size:
- *Height.*—28 cm.
- *Width.*—15 cm.

Flower:
- *Type.*—Perfect. Complete.
- *Shape.*—Campanulate.
- *Size.*—6 mm. wide and 5 mm. deep.
- *Petal count.*—5.
- *Petal size.*—2.5 mm. long and less than 1 mm. wide.
- *Petal shape.*—Lanceolate with a clawed base.
- *Petal texture.*—Satiny.
- *Calyx.*—5 parted.
- *Calyx shape.*—Campanulate, fused from receptacle to about half-way to sepal tip.
- *Calyx size.*—4 mm wide and 5 mm deep.
- *Calyx texture.*—Pubescent (glandular when seen under a microscope).
- *Ovary position.*—Superior.
- *Carpel number.*—2.
- *Stamens.*—Sterile.
- *Stamen number.*—5.
- *Inflorescence type.*—Panicle.
- *Flower number per inflorescence.*—50–100.
- *Peduncle width.*—3–4 mm tapering to 1 mm.
- *Peduncle texture.*—Villous.
- *Blooming height.*—60 cm.
- *Bloom period.*—June–July.
- *Fragrance.*—None.

Fruit:
- *Type.*—Dehiscent capsule.
- *Fertility.*—Moderate fertility.
- *Fruit size.*—About 2 mm long and wide.
- *Seed size.*—Minute (dust-like).
- *Seed shape.*—Elliptic to obovate.

Habit: Clumping.

Disease: None observed on plants grown in Canby, Oreg.

Hardiness: Cold hardy to USDA Zone 5.

Color characteristics:
- *Foliage.*—Mature: Upper surface — RHS 198A Greyed-Green Group. Upper surface, along veins —

Close to RHS 147A Yellow-Green Group but darker. Lower surface — Close to RHS 187A Greyed-Purple Group. Immature: Upper surface — RHS 197A Greyed-Green Group.

*Flower.*—Bud — RHS 54B Red Group. Petals — RHS 55D White Group. Calyx — RHS 54C Red Group. Ovary — RHS 11C Yellow Group. Anther — RHS 199A Grey-Brown Group to RHS 200D Brown Group.

*Fruit.*—Fresh — RHS 54C Red Group.

*Seed.*—Dry — RHS 202A Black Group.

*Peduncle.*—RHS 183B Greyed-Purple Group.

*Pedicel.*—RHS 183B Greyed-Purple Group.

DESCRIPTION OF PARENT PLANTS

The instant plant resulted from a cross between Heuchera 'French Velvet' and an unnamed Heuchera hybrid seedling. Heuchera 'French Velvet' was selected as a parent plant for its felted leaves (underside and petioles) and foliage color. The instant plant differs from Heuchera 'French Velvet' in having substantially more silver veiling, shorter leaf hairs, and shorter petioles. The Heuchera hybrid seedling was selected for its silver veiling and compact form. The instant plant differs from the Heuchera hybrid seedling in having a sharper leaf appearance (margins are more dentate) and hairier petioles and leaf underside.

I claim:

1. A new and distinct hybrid of Heuchera plant substantially as shown and described, characterized by a unique combination of mint green leaves with a pinkish cast and compact form as a result of short petioles.

* * * * *

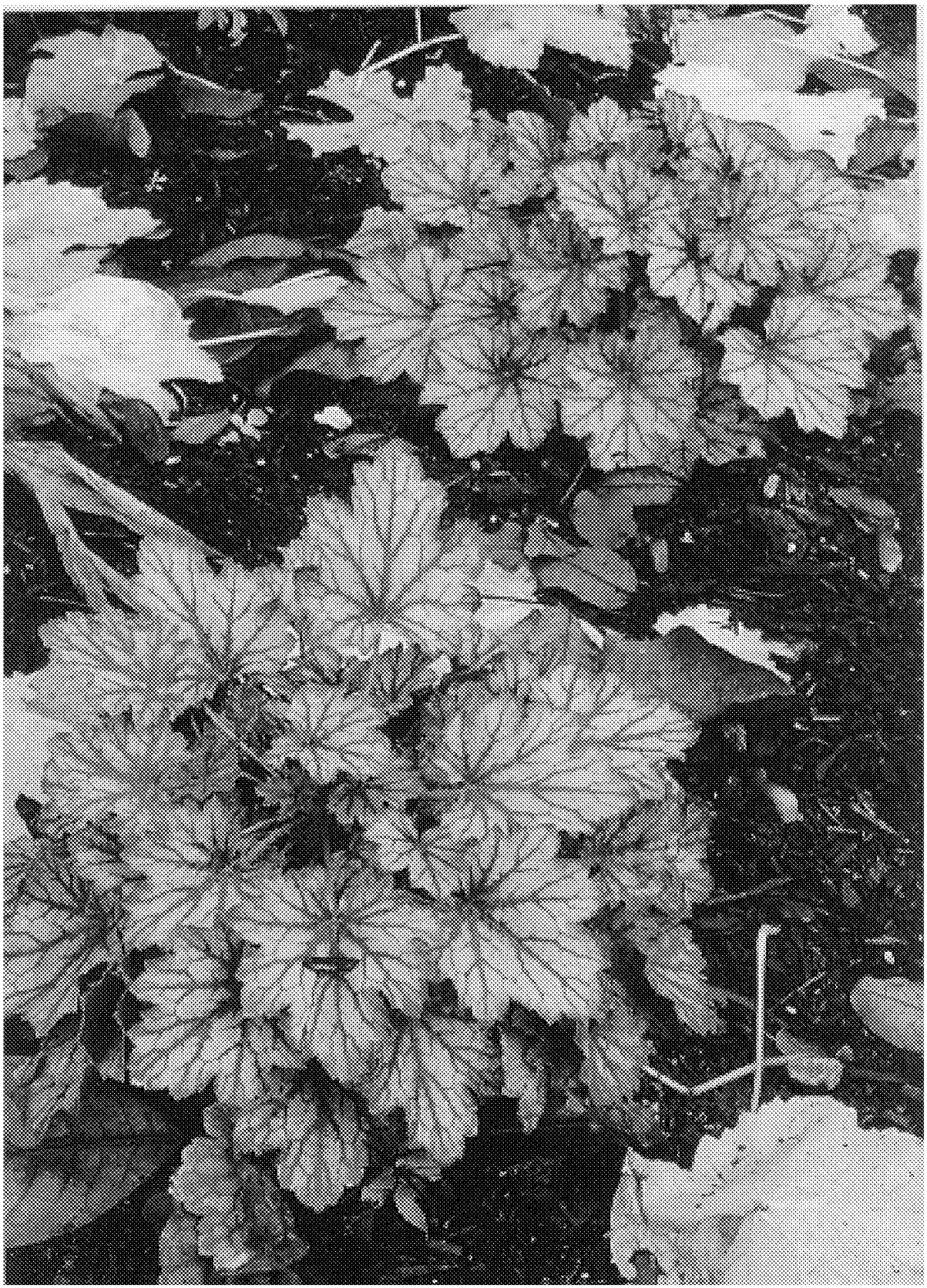

UNITED STATES PATENT AND TRADEMARK OFFICE

CERTIFICATE OF CORRECTION

PATENT NO. : PP 12,160 P2
DATED : October 23, 2001
INVENTOR(S) : Heims

It is certified that error appears in the above-identified patent and that said Letters Patent is hereby corrected as shown below:

Title page,
Item [54], the word "HUECHERA" is mis-spelled. It should read -- HEUCHERA --.

Signed and Sealed this

Fourth Day of March, 2003

JAMES E. ROGAN
*Director of the United States Patent and Trademark Office*